(12) United States Patent
Embree et al.

(10) Patent No.: US 11,819,536 B2
(45) Date of Patent: Nov. 21, 2023

(54) SUSTAINED RELEASE COMPOSITIONS AND METHODS FOR TREATMENT OF TEMPOROMANDIBULAR JOINT DEGENERATION

(71) Applicant: The Trustees of Columbia University in the City of New York, New York, NY (US)

(72) Inventors: Mildred Embree, New York, NY (US); Mo Chen, Rochester, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 119 days.

(21) Appl. No.: 17/253,993

(22) PCT Filed: Jun. 19, 2019

(86) PCT No.: PCT/US2019/037869
§ 371 (c)(1),
(2) Date: Dec. 18, 2020

(87) PCT Pub. No.: WO2019/246179
PCT Pub. Date: Dec. 26, 2019

(65) Prior Publication Data
US 2021/0268067 A1 Sep. 2, 2021

Related U.S. Application Data

(60) Provisional application No. 62/688,545, filed on Jun. 22, 2018.

(51) Int. Cl.
| | | |
|---|---|---|
| *A61K 31/18* | (2006.01) | |
| *A61K 38/18* | (2006.01) | |
| *A61K 47/61* | (2017.01) | |
| *A61K 47/64* | (2017.01) | |
| *A61K 9/06* | (2006.01) | |
| *A61K 9/50* | (2006.01) | |
| *A61K 31/728* | (2006.01) | |

(52) U.S. Cl.
CPC ............ *A61K 38/18* (2013.01); *A61K 9/06* (2013.01); *A61K 9/5031* (2013.01); *A61K 31/728* (2013.01); *A61K 47/61* (2017.08); *A61K 47/64* (2017.08)

(58) Field of Classification Search
None
See application file for complete search history.

(56) References Cited

U.S. PATENT DOCUMENTS

| | | | | |
|---|---|---|---|---|
| 6,096,728 A | * | 8/2000 | Collins | ............... A61K 31/00 514/62 |
| 6,528,097 B1 | | 3/2003 | Vaughn et al. | |
| 2010/0028335 A1 | | 2/2010 | Lu et al. | |
| 2016/0193299 A1 | | 7/2016 | de Fougerolles et al. | |

FOREIGN PATENT DOCUMENTS

| | | |
|---|---|---|
| JP | 2001500472 A | 1/2001 |
| WO | 9728828 A1 | 8/1997 |

OTHER PUBLICATIONS

Embree et al (Exploiting endogenous fibrocartilage stem cells to regenerate cartilage and repair joint injury. Nature Communications. 7:13073. 2016, p. 1-13) (Year: 2016).*
Dashnyam et al (Intra-articular biomaterials-assisted delivery to treat temporomandibular joint disorders. Journal of Tissue Engineering. vol. 9: 1-12 (published online May 13, 2018) (Year: 2018).*
Torstrick, et al., "Local Strategies to Prevent and Treat Osteoporosis", Current Osteoporosis Reports, Springer US, New York, vol. 12, No. 1, Feb. 11, 2014 (Feb. 11, 2014), pp. 33-40, XP035363551.
European Search Report dated Feb. 10, 2022 for corresponding EP Application No. 19 82 3612.7.
Chinese Office Action dated May 25, 2022, in connection with corresponding CN Application No. 201980054589.4 (20 pp., including machine-generated English translation).
International Search Report for PCT Application No. PCT/US2019/037869 dated Oct. 15, 2019.
Written Opinion for PCT Application No. PCT/US2019/037869 dated Oct. 15, 2019.
Embree MC, et al., "Exploiting Endogenous Fibrocartilage Stem Cells to Regenerate Cartilage and Repair Joint Injury" Nature Communications Oct. 10, 2016 DOI: 10.1038/ncomms13073 (pp. 1-13); abstract; p. 2, right column, top paragraph; p. 8, left column.
Haynes KR, et al. "Treatment of Mouse Model of Ankylosing Spondylitis with Exogenous Sclerostin has no Effect on Disease Progression" BMC Musculoskeletal Disorders 2015, 16:368 (pp. 1-8); abstract.
Makadia, et al., "Poly Lactic-co-Glycolic Acid (PLGA) as Biodegradable Controlled Drug Delivery Carrier" National Center for Biotechnology Information, Sep. 1, 2011; 3(3): (pp. 1377-1397); https://www.ncbi.nlm.nih.gov/pmc/articles/PMC3347861/.
Koda et al., "Development of Poly Lactic/Glycolic Acid (PLGA) Microspheres for Controlled Release of Rho-Associated Kinase Inhibitor" Journal of Ophthalmology, vol. 2017, Article ID 1598218; https://www.hindawi.com/journals/joph/2017/1598218/.
Wu et al., "Insulin-loaded PLGA microspheres for glucose-responsive release" Drug Delivery, vol. 24, 2017—Issue 1; https://www.tandfonline.com/doi/full/10.1080/10717544.2017.1381200.
Manfredini, et al., "Hyaluronic acid in the treatment of TMJ disorders: a systematic review of the literature" Pub Med, Jul. 10, 2010, DOI: 10.1179/crn.2010.023 ; abstract.

(Continued)

*Primary Examiner* — Jake M Vu

(74) *Attorney, Agent, or Firm* — McCormick, Paulding & Huber PLLC

(57) ABSTRACT

A composition for treating TMJ degeneration comprising a hydrogel of sclerostin and high molecular weight hyaluronic acid, or PLGA-encapsulated sclerostin, or sclerostin covalently linked to hyaluronic acid.

7 Claims, 8 Drawing Sheets

(56) References Cited

OTHER PUBLICATIONS

Kim, Chang-Hwan, et al "Therapeutic Effect of Hyaluronic Acid on Experimental Osteoarthrosis of Ovine Temporomandibular Joint", Journal of Veterinary Medical Science, 2001, vol. 63, No. 10, pp. 1083-1089.
Japanese Office Action and its English translation dated Feb. 1, 2022 for corresponding JP Application No. 2020-571508.

* cited by examiner

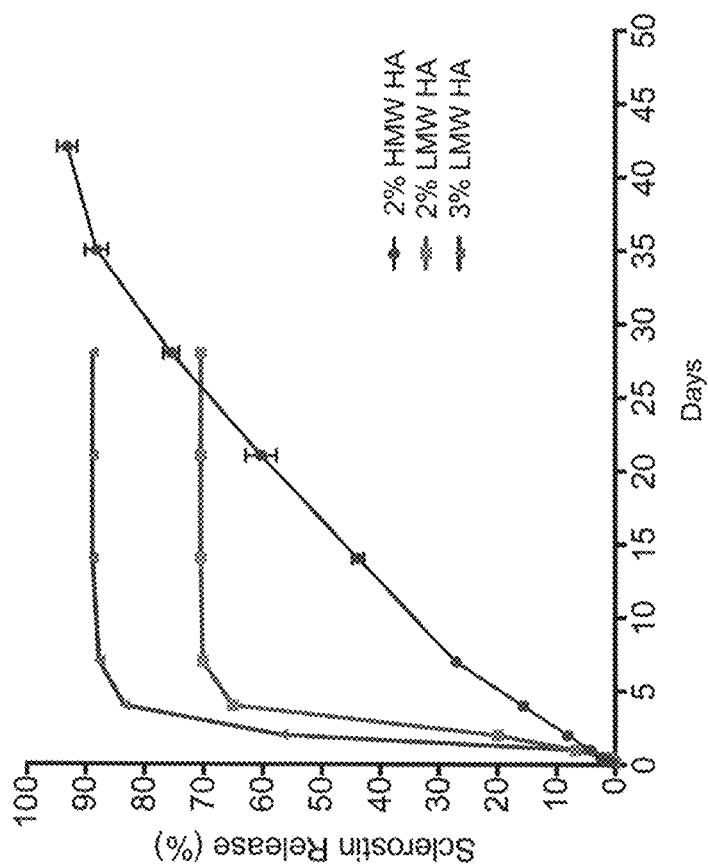

Fig. 1. Release curve shows that high molecular weight hyaluronic acid-sclerostin hydrogel has sustained release of sclerostin over 42 days. Sclerostin (1 µg) was mixed in 2% high molecular weight hyaluronic acid (HMW HA, 2×10$^6$ KDa) or in 2% and 3% low molecular weight (LMW HA, 500 KDa). The hydrogels were incubated in PBS at 37°C. The concentration of sclerostin was measured at each indicated time point using ELISA to plot the cumulative release curves.

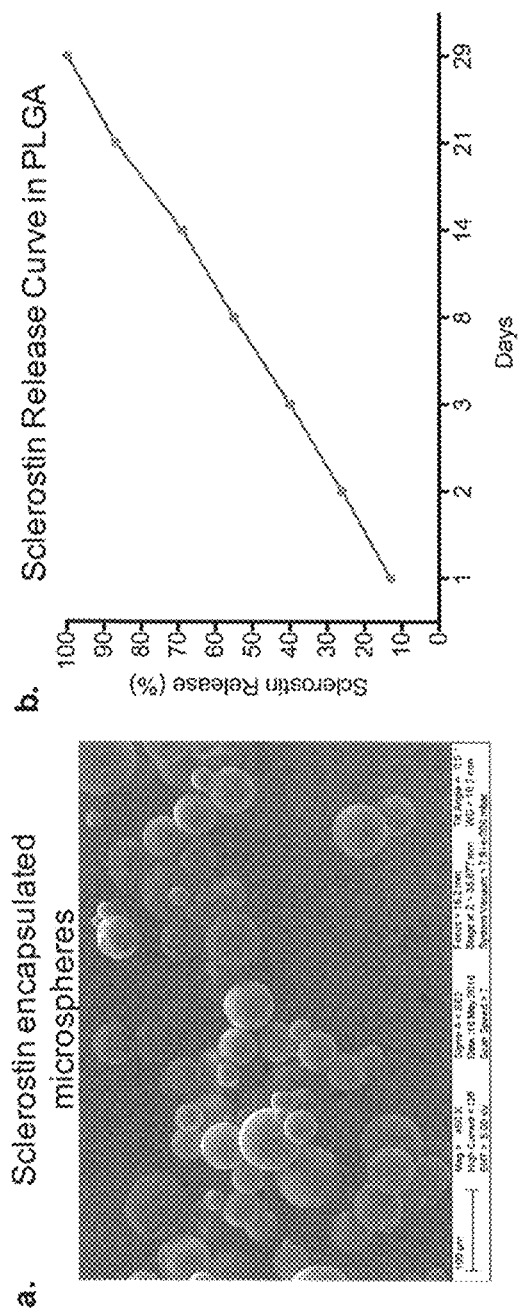

Fig. 2. Release curve shows that sclerostin microspheres has sustained release of sclerostin over a one month period. (a) Sclerostin (1 μg) was encapsulated with PLGA microspheres. Scale bar=100mm. (b) The PLGA sclerostin microspheres were placed on Transwells in PBS at 37°C. The concentration of sclerostin was measured at each indicated time point using ELISA to plot the cumulative release curves.

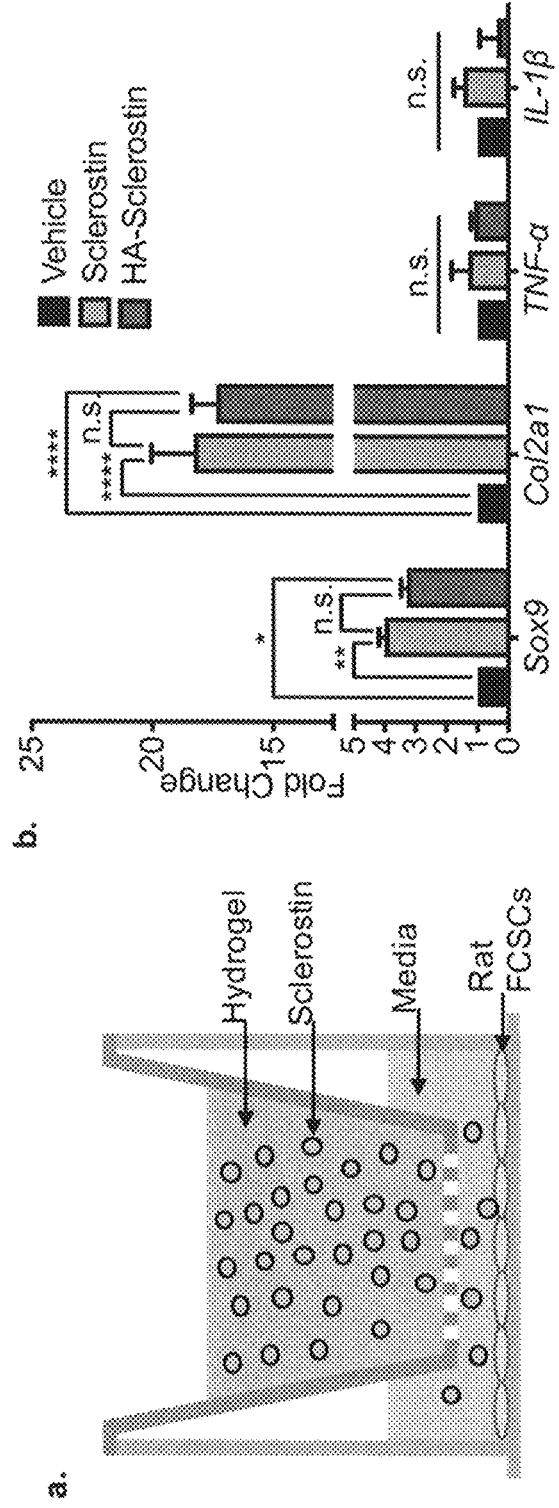

Fig. 3. Hyaluronic acid-sclerostin hydrogel induces differentiation, but does not cause inflammation in rat FCSCs. (a) Sclerostin was mixed in 2% high molecular weight hyaluronic acid (HMW HA), placed in a Transwell, and cultured with rat FCSCs in media containing 2% FBS for one week. Rat FCSCs treated with sclerostin (50 ng/ml) or vehicle served as controls. (b) After 1 week, qRT-PCR shows cartilage-related genes Sox9 and Col2a1 are increased in HA-sclerostin hydrogel similar to sclerostin alone, while inflammatory cytokine genes TNF-α and IL-1β are unchanged in FCSCs treated with HA-sclerostin hydrogel. Data are normalized to Gapdh and mean fold change relative to vehicle ± SD; n=3.

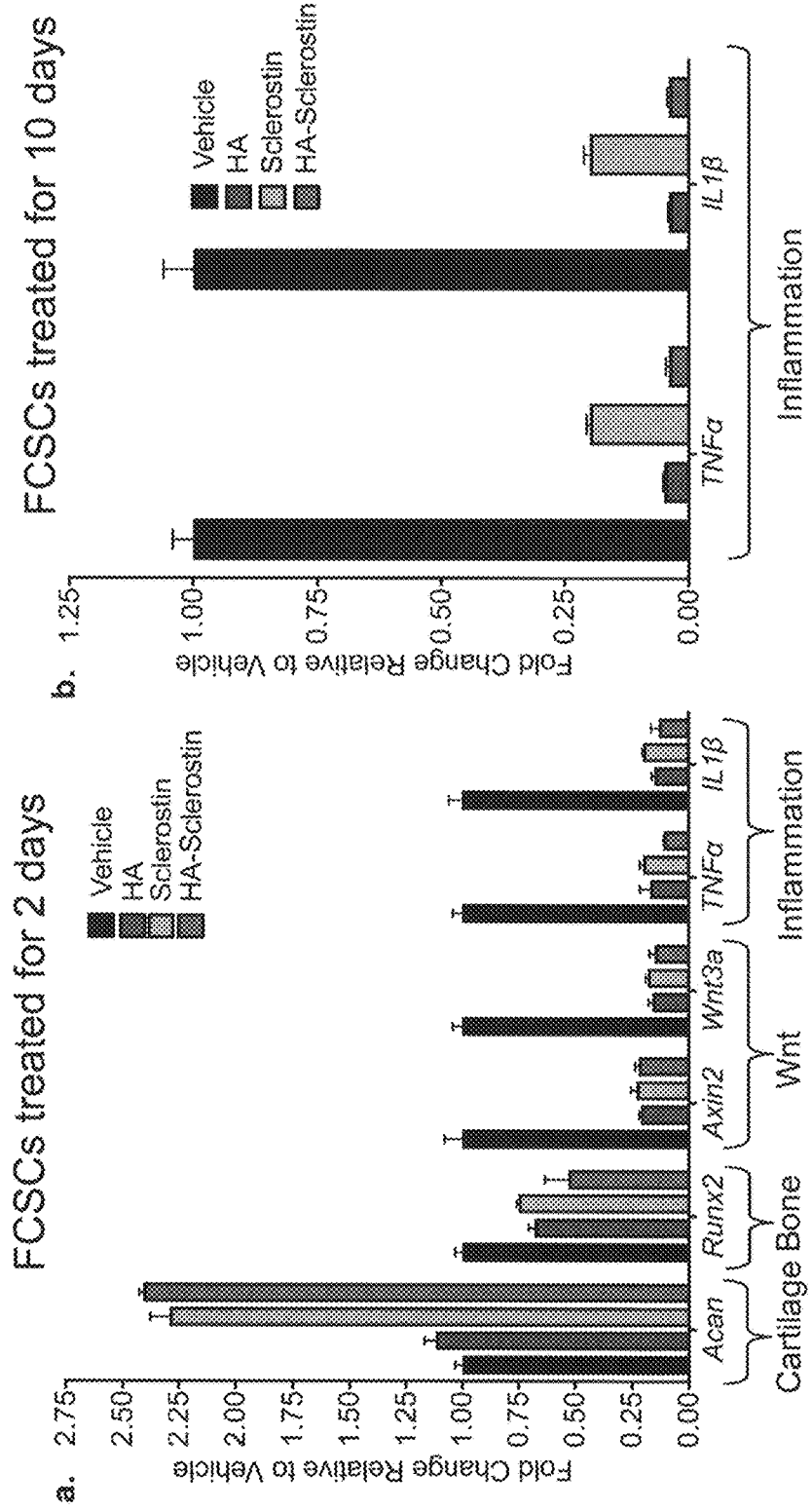

Fig.4. Hyaluronic acid-sclerostin hydrogel induces FCSCs to differentiation into cartilage similar to sclerostin treated FCSCs, and reduces inflammation in TMJ fibrocartilage stem cells (FCSCs). (a) Sclerostin (1μg) was mixed in 2% high molecular weight hyaluronic acid (HMW HA, 2x10⁶ KDa), placed in a Transwell, and cultured with rat fibrocartilage stem cells (FCSCs) in media containing 2% FBS. Rat FCSCs treated with HMW HA (2x10⁶ KDa), sclerostin (50 ng/ml), or vehicle PBS served as controls. After 2 days (a) qRT-PCR shows cartilage-related gene (Acan) is increased in HA-sclerostin hydrogel similar to sclerostin alone, while bone marker (Runx2), Wnt targets (Wnt3a, Axin2), inflammatory cytokine genes (TNF-α, IL-1β) are reduced in FCSCs treated with HA-sclerostin hydrogel. Data are normalized to Gapdh and mean fold change relative to vehicle ± SD. (b) qRT-PCR shows after 10 days in culture FCSCs have decrease in inflammatory cytokine genes TNF-α and IL-1β when treated with HA-sclerostin hydrogel, relative to vehicle and Sclerostin alone. Data are normalized to Gapdh and mean fold change relative to vehicle ± SD.

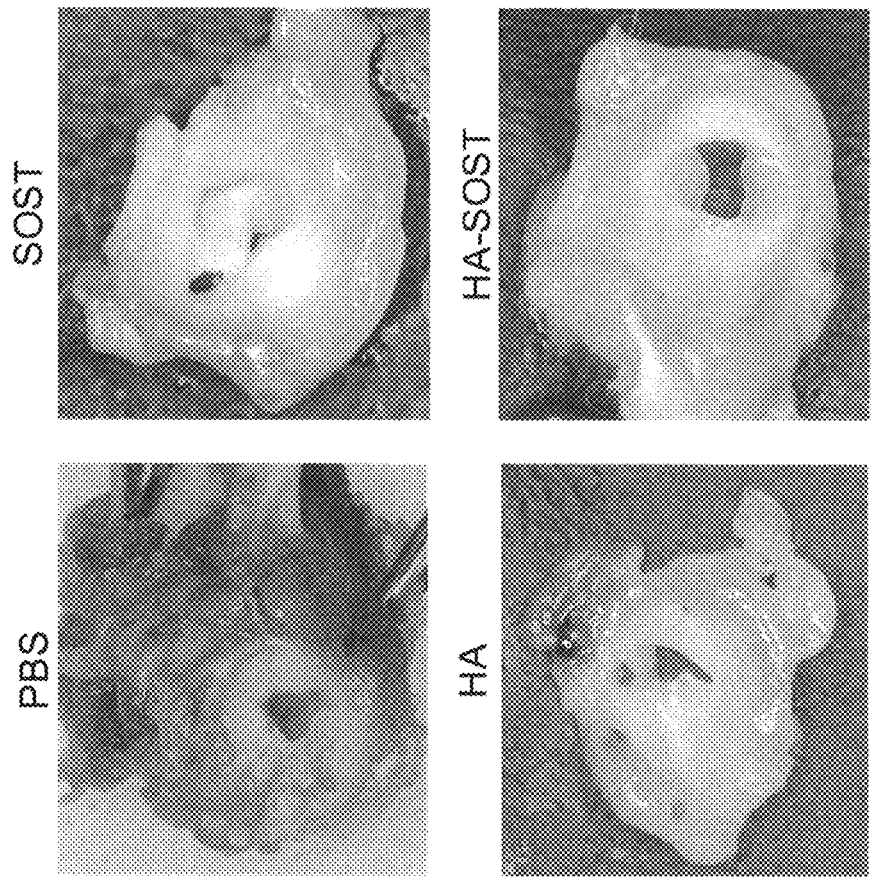

Fig 5. Hyaluronic acid-sclerostin hydrogel heals TMJ disc perforation in rabbit injury model. TMJ osteoarthritis was surgically induced bilaterally in a New Zealand white rabbits by creating a 2.5 mm perforation in the TMJ disc. A total of 6 rabbits were equally divided into two treatment groups: 1) Unilateral HA-SOST injection (1μg in 2% HMW HA, $2\times10^6$ KDa), and unilateral (2% HMW HA, $2\times10^6$ Kda) injection on contralateral side biweekly; 2) Unilateral Sclerostin injection (50ng/ml) and PBS injection on contralateral week following injury. Rabbit condyles are currently being processed for histology.

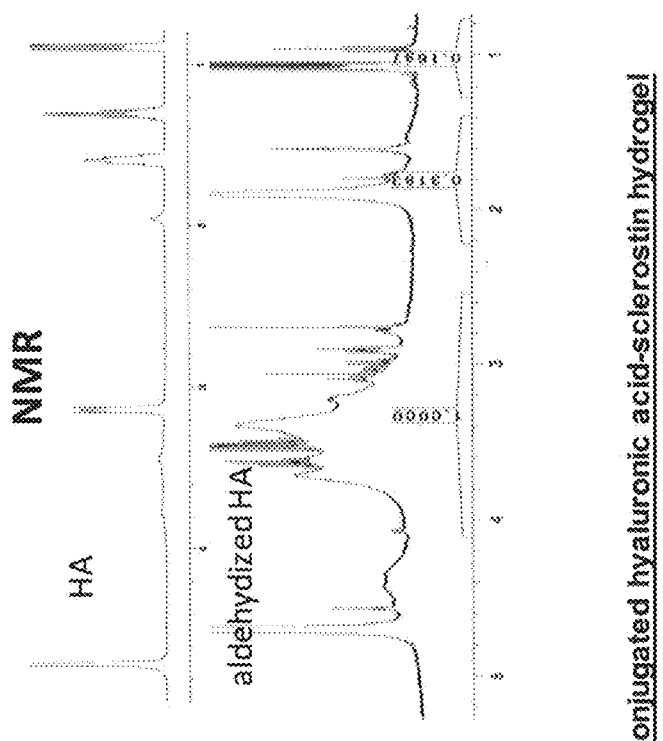
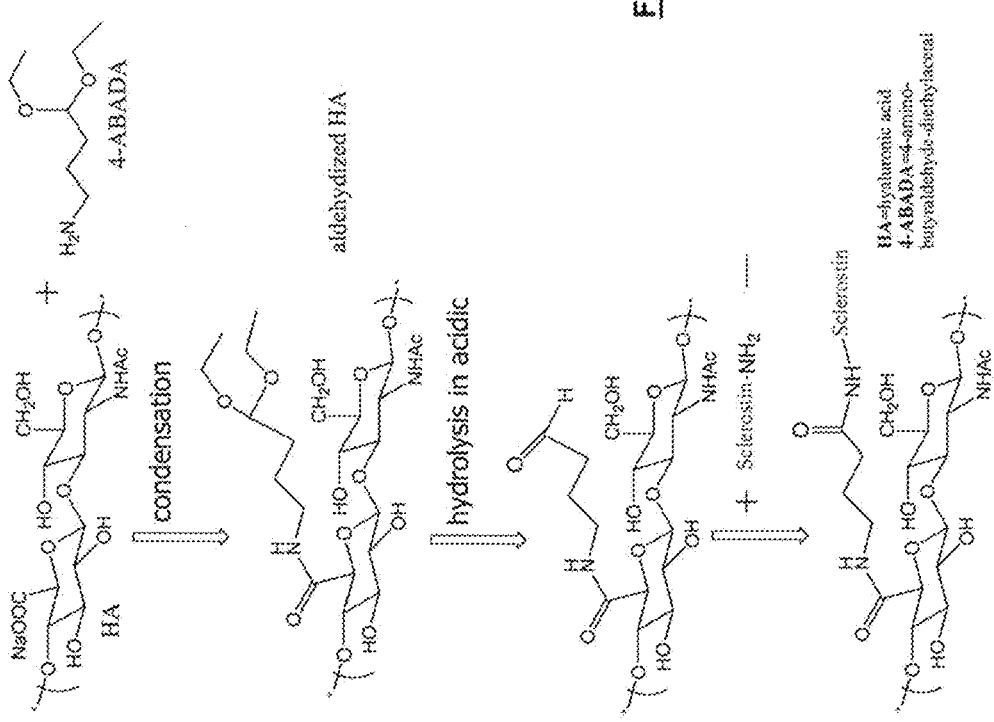
Fig. 6. Formulation of conjugated hyaluronic acid-sclerostin hydrogel

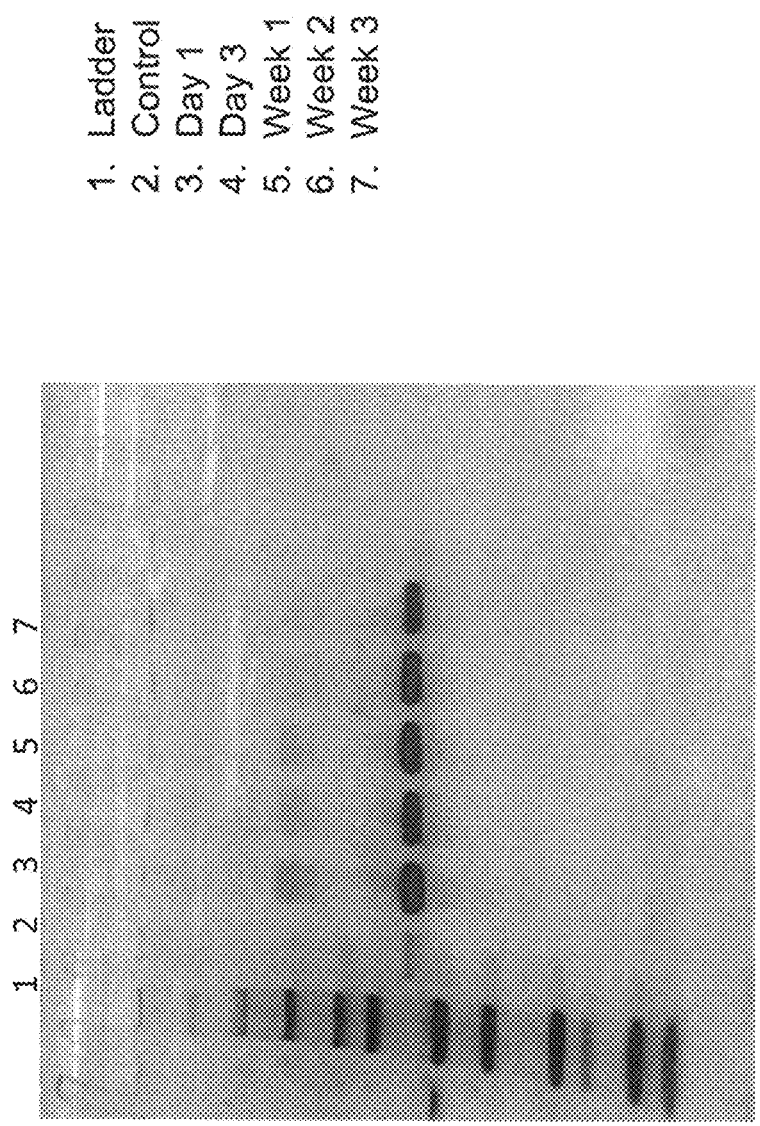
Fig 7. SOST stability in HMW-HA. SOST released from high molecular weight HA (incubated at 37 degree) was harvested at different time points and the samples was loaded to a 4-12% SDS page gel. Proteins on the gel was stained with Pierce Silver Staining Kit (Thermofisher).

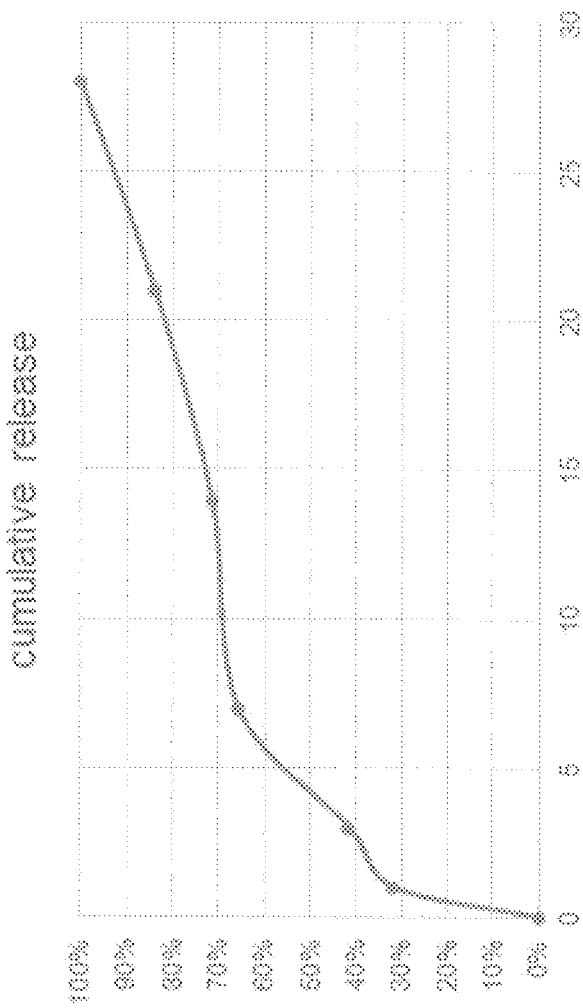

Fig 8. SOST sustained release from the SOST-HA covalent conjugated hydrogel. 10μg covalently conjugated HA-SOST was dissolved in 0.5 ml PBS. At each indicated time points, 0.25 ml solution (supernatant) was collected and equal amount of PBS was added back. 10μl of each sample was diluted in 200μl diluent buffer from ELISA kit, and measured using the Sclerostin (SOST) Human ELISA Kit (Thermofisher)

SUSTAINED RELEASE COMPOSITIONS AND METHODS FOR TREATMENT OF TEMPOROMANDIBULAR JOINT DEGENERATION

CROSS-REFERENCE TO RELATED APPLICATIONS

This application is a National Stage Application of International Patent Application No. PCT/US2019/037869 filed on Jun. 19, 2019, which claims priority from U.S. provisional patent application 62/688,545, filed Jun. 22, 2018, each of which is incorporated herein by reference in its entirety.

GOVERNMENT RIGHTS

This invention was made with government support under DE022060 awarded by the National Institutes of Health. The government has certain rights in the invention.

TECHNICAL FIELD

The present invention relates to compositions and methods for treatment of degeneration of the temporomandibular joint (TMJ), including TMJ osteoarthritis.

BACKGROUND

The following discussion is provided merely to aid the reader in understanding the disclosure and is not admitted to describe or constitute prior art thereto.

The temporomandibular joint (TMJ) is a complex joint system critical for dental occlusion, mastication, respiration, and speech. The TMJ is comprised of a network of muscles, ligaments, and a fibrocartilaginous disc and condyle. TMJ trauma and degenerative diseases, including TMJ osteoarthritis (OA), are debilitating and compromise quality of life. TMJ diseases afflict over 10 million Americans at an annual cost of ~$4 billion and are one of the research priorities of the National Institute of Dental and Craniofacial Research. Current treatments for TMJ OA are typically one of two extremes—either palliative pain management or invasive surgeries. Surgeries include total joint replacements, which have high failure rates. There is a paucity of minimally invasive and directed TMJ therapies that target pathological mechanisms and promote innate tissue regeneration.

Anatomically the TMJ condyle fits into the glenoid fossa of the temporal bone. The disc divides the joint space into the inferior and superior joint cavity, which facilitate rotational and translational mechanics, respectively. A fibrous membrane called the joint capsule surrounds the entire TMJ and completely encloses both joint cavities. The articulating surface of the condyle and disc are comprised of fibrocartilage. Unlike hyaline cartilage, fibrocartilage consists of both fibrous and cartilaginous tissues, which provide tensile and compressive strength, respectively. The TMJ condyle undergoes endochondral ossification, in which cartilage anlagen are resorbed and replaced by bone. Condyle growth is marked by well-defined zones of cellular maturation, including the superficial zone (SZ) harboring fibrocartilage stem cells (FCSCs), polymorphic zone (PM) containing heterogeneous cells, maturation zone (MZ) harboring chondrocytes, hypertrophic zone (HZ) harboring terminally differentiated hypertrophic chondrocytes, and the erosive zone (EZ) where cartilage is resorbed and bone is formed.

Fibrocartilage stem cells (FCSCs) residing in the TMJ condyle superficial zone (SZ) self-organize, engraft into injured tissue and regenerate both cartilage and vascularized bone. Wnt/Catenin signals induce proliferation and inhibit differentiation of FCSCs, while over-active Wnt/Catenin signals deplete FCSCs and cause TMJ OA.

Hyaluronic acid (HA) is a non-sulfated glycosaminoglycan broadly found in the extracellular matrices of connective tissues. HA is naturally present in cartilage and joint synovial fluid and plays multiple, critical functions in joint health. Long chains of HA are essential for linking proteoglycan aggregates in cartilage, providing structural support for joint mechanics. HA also forms complexes with lubricin and contributes to joint lubrication. In synovial fluid, HA mediates both anti-nociceptive and anti-inflammatory actions. Moreover, intra-articular injections of HA hydrogels are FDA-approved for the treatment of knee osteoarthritis. HA hydrogels are biodegradable, non-immunogenic, and have been used to encapsulate growth factors and molecules, providing sustained release for weeks.

Injection of hyaluronic acid has been explored as a possible treatment for TMJ OA but results have been inconclusive.

Poly (DL lactic-co-glycolic acid) (PLGA) is a polyester copolymer formed by copolymerizing glycolic acid and lactic acid (or sometimes by copolymerizing the respective cyclic lactones glycolide and lactide). PLGA is sometimes also referred to as poly (DL-lactide-co-glycolide). PLGA has been used for delivery of active agents to patients. See, for example, Makadia et al.—Polymers (Basel). 2011 Sep. 1; 3(3): 1377-1397. https://www.ncbi.nlm.nih.gov/pmc/articles/PMC3347861/; Koda et al.—Journal of Ophthalmology, Volume 2017, Article ID 1598218, https://www.hindawi.com/journals/joph/2017/1598218/; and Wu et al.—Drug Delivery Volume 24, 2017—Issue 1 https://www.tandfonline.com/doi/full/10.1080/10717544.2017.1381200, which are incorporated herein by reference in their entirety. PLGA is commercially available from (for example) Sigma-Aldrich.

Exploiting the regenerative capabilities of resident stem cells to repair TMJ tissues represents a minimally invasive stem cell-based treatment for TMJ OA. TMJ fibrocartilage stem cells (FCSCs) reside in the TMJ condyle superficial zone. Transplanted FCSCs self-organize, regenerate cartilage and vascularized bone, and engraft into injured host tissue. See Embree et al.—"Exploiting endogenous fibrocartilage stem cells to regenerate cartilage and repair joint injury"—Nature Commun. DOI:10.1038/ncomms13073 (2016), which is incorporated herein by reference in its entirety.

Given the restricted number of cells and lack of vascular supply, cartilage has poor regenerative properties. Thus TMJ injury and chronic degenerative disease, including TMJ osteoarthritis (OA), can cause pain, dysfunction, and irreversible loss of tissue. Clinical treatments for TMJ trauma/degeneration are limited and involve either palliative care or invasive surgical interventions that often fail or cause further damage. Minimally invasive cell-based therapies that promote TMJ regeneration are not available clinically. Making such a therapy available to the medical community would be a significant benefit to sufferers with TMJ degeneration such as TMJ OA.

SUMMARY

Provided herein are sustained release compositions for treatment of TMJ degeneration comprising: 1) sclerostin and high molecular weight hyaluronic acid or 2) sclerostin encapsulated in PLGA, or 3) sclerostin covalently linked to high molecular weight hyaluronic acid. Also provided are methods of treating said TMJ degeneration in a patient in need of such treatment by administration of a therapeutically-effective amount of one of the sustained release composition.

The compositions comprise a therapeutically-effective concentration of sclerostin, which may range from 5 ng/100 µl to about 1 mg/100 µl sclerostin and from about 0.1 to about 10 wt % high molecular weight hyaluronic acid or PLGA preferably from about 50 ng/100 µl to about 5 µg/100 µl sclerostin and from about 0.5 to about 5 wt % high molecular weight hyaluronic acid or PLGA, and more preferably about 1 µg/100 µl sclerostin and about 2 wt % high molecular weight hyaluronic acid or PLGA. A therapeutically-effective amount of sclerostin to be delivered by one of the subject compositions is preferably from 10 ng to 10 µg, but other amounts may be administered as will be understood by those skilled in the treatment art.

Preferred sustained release compositions of the invention consist essentially of: 1) sclerostin and high molecular weight hyaluronic acid or 2) sclerostin encapsulated in PLGA, or 3) sclerostin covalently linked to hyaluronic acid.

The described compositions may be administered as understood in the art, normally by injection into the TMJ. See, for example, Manfredini et al.—Cranio. 2010 July; 28(3):166-76 https://www.ncbi.nlm.nih.gov/pubmed/20806734, which is incorporated herein in its entirety.

The foregoing general description and following detailed description are exemplary and explanatory and are intended to provide further explanation of the invention.

BRIEF DESCRIPTION OF THE DRAWINGS

FIG. 1 is a release curve for sclerostin from a sclerostin-hyaluronic acid hydrogel.

FIG. 2 is a release curve for sclerostin from a PLGA-encapsulated sclerostin formulation FIG. 3 shows in vitro evaluation of a hyaluronic acid-sclerostin hydrogel for activity against rat FCSCs.

FIG. 4 is a comparison of activities of HA-sclerostin and the individual components of the composition.

FIG. 5 shows the activity of the HA-sclerostin hydrogel in a rabbit injury model FIG. 6 shows the synthetic scheme for a conjugated sclerostin-HA composition.

FIG. 7 shows gel staining of sclerostin released from a sclerostin-hyaluronic acid hydrogel.

FIG. 8 is a release curve of sclerostin from a conjugated sclerostin-HA composition.

DETAILED DESCRIPTION

In accordance with the present invention, a composition is provided for treatment of TMJ degeneration, particularly TMJ osteoarthritis, which comprises a hydrogel of high molecular weight hyaluronic acid and sclerostin. The composition preferably consists essentially of high molecular weight hyaluronic acid and sclerostin. Also provided is a method of treating TMJ degeneration (and particularly TMJ osteoarthritis) in a patient in need of such treatment which comprises injecting a therapeutically-effective amount of the sclerostin-hyaluronic acid hydrogel into the temporomandibular joint. The composition may comprise (or consist essentially of) from about 5 ng/100 µl to about 1 mg/100 µl sclerostin and from about 0.1 to about 10 wt % high molecular weight hyaluronic acid, preferably from about 50 ng/100 µl to about 5 µg/100 µl sclerostin and from about 0.5 to about 5 wt % high molecular weight hyaluronic acid, and more preferably about 1 µg/100 µl sclerostin and about 2 wt % high molecular weight hyaluronic acid. In the compositions that consist essentially of sclerostin and high molecular weight hyaluronic acid, the remainder of the composition is one or more solvents, carriers, and the like.

In another embodiment of the present invention, a composition is provided for treatment of TMJ degeneration, particularly TMJ osteoarthritis, which comprises a PLGA-encapsulated sclerostin formulation. The composition of this embodiment preferably consists essentially of PLGA-encapsulated sclerostin. Also provided in this embodiment is a method of treating TMJ degeneration (and particularly TMJ osteoarthritis) in a patient in need of such treatment which comprises injecting a therapeutically-effective amount of the PLGA-encapsulated sclerostin into the temporomandibular joint. The composition may comprise (or consist essentially of) from 5 ng/100 µl to about 1 mg/100 µl sclerostin and from about 0.1 to about 10 wt % PLGA, preferably from about 50 ng/100 µl to about 5 µg/100 µl sclerostin and from about 0.5 to about 5 wt % PLGA, and more preferably about 1 µg/100 µl sclerostin and about 2 wt % PLGA. In the compositions that consist essentially of sclerostin and PLGA, the remainder of the composition is one or more solvents, carriers, and the like.

The PLGA used in the claimed compositions is preferably a 50:50 copolymer having an average molecular weight of about 30,000 to 60,000 Da, but copolymers having other ratios of monomers and other molecular weight ranges may be used as would be understood in the art, including 85:15, 65:35, and 75:25 lactic acid/glycolic acid and an average molecular weight from about 7000 to about 240,000 Da.

In another embodiment of the present invention, a composition is provided for treatment of TMJ degeneration, particularly TMJ osteoarthritis, which comprises a composition comprising sclerostin covalently linked to high molecular weight hyaluronic acid. The composition of this embodiment preferably consists essentially of sclerostin covalently linked to hyaluronic acid. Also provided is a method of treating TMJ degeneration (and particularly TMJ osteoarthritis) in a patient in need of such treatment which comprises injecting a therapeutically-effective amount of the sclerostin-linked hyaluronic acid into the temporomandibular joint. The composition may comprise (or consist essentially of) from about 5 ng/100 µl to about 1 mg/100 µl sclerostin and from about 0.1 to about 10 wt % high molecular weight hyaluronic acid, preferably from about 50 ng/100 µl to about 5 µg/100 µl sclerostin and from about 0.5 to about 5 wt % high molecular weight hyaluronic acid, and more preferably about 1 µg/100 µl sclerostin and about 2 wt % high molecular weight hyaluronic acid. In the compositions that consist essentially of sclerostin and high molecular weight hyaluronic acid, the remainder of the composition is one or more solvents, carriers, and the like.

In the composition embodiment comprising (or consisting essentially of) sclerostin covalently linked to hyaluronic acid, the linking may be accomplished by using a suitable linking agent to link the sclerostin to the hyaluronic acid through an amine group of sclerostin and the carboxyl group of the high molecular weight hyaluronic acid, as is well understood in the chemical art. The linking may be performed, for example, by reacting an amine-containing linker having a free aldehyde group with hyaluronic acid to form an amide bond with the carboxylic acid group of the hyaluronic acid, followed by hydrolysis of the acetal group to a free carboxylic acid group and then linking sclerostin to the free carboxyl group via a cyanoborohydride salt. A preferred linking agent is 4-aminobuteraldehyde-diethylacetal (4-ABADA), but other suitable linking agents may be used, as is known in the art. See, for example, Du et al.—Biomacromolecules 2014, 15, 1097-1114. Suitable linkers are readily available from scientific supply companies such as (for example) Sigma-Aldrich.

It is to be understood that the claimed compositions and methods are not limited to the particular embodiments described, and as such may vary. It is also to be understood that the terminology used herein is for the purpose of describing particular embodiments only, and is not intended to be limiting. The scope of the present technology will be limited only by the appended claims.

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "about" means plus or minus 10%.

As used herein, "optional" or "optionally" means that the subsequently described event or circumstance may or may not occur, and that the description includes instances where said event or circumstance occurs and instances where it does not.

As used herein, the terms "individual", "patient", or "subject" can be an individual organism, a vertebrate, a mammal (e.g., a bovine, a canine, a feline, or an equine), or a human. In a preferred embodiment, the individual, patient, or subject is a human.

As used herein, the phrases "therapeutically effective amount" and "therapeutic level" mean a dose or plasma concentration of a therapeutic material in a subject or patient that provides the specific pharmacological effect for which the material is administered in a subject or patient in need of such treatment, i.e., to reduce, ameliorate, or eliminate TMJ degeneration. It is emphasized that a therapeutically effective amount or therapeutic level of a drug will not always be effective in treating TMJ degeneration, even though such dosage is deemed to be a therapeutically effective amount by those of skill in the art. The therapeutically effective amount may vary based on the age and weight of the subject, and/or the subject's condition. A therapeutically-effective amount of sclerostin to be delivered by one of the subject compositions is preferably from 10 ng to 10 µg, but other amounts may be administered as will be understood by those skilled in the treatment art.

The terms "treatment" or "treating" as used herein with reference to TMJ degeneration or TMJ osteoarthritis refer to reducing, ameliorating or eliminating one or more symptoms or effects of the disease or condition. See, for example, Kalladka et al.—J. Indian Prosthodont. Soc (January-March 2014) 14 (1): 6-15, which is incorporated herein in its entirety.

A "therapeutic response" means an improvement in at least one measure of TMJ degeneration.

As used herein, the term "high molecular weight hyaluronic acid" or "HMW HA" means hyaluronic acid having an average molecular weight of more than about 800 kDa, preferably from about 800 to about 8000 kDa, more preferably from about 1000 to about 6000 kDa, more preferably from about 1500 to about 4000 kDa, and most preferably about 2000 kDa, while the term "low molecular weight hyaluronic acid" or "LMW HA" means hyaluronic acid having an average molecular weight less than about 800 kDa, preferably from about 100 to about 800 kDa, and most preferably about 500 kDa.

The following abbreviations may be used herein: bovine serum albumin (BSA), phosphate buffered saline (PBS), sclerostin (SOST), poly lactic acid-glycolic acid (PLGA), polyvinyl alcohol (PVA), hyaluronic acid (HA), temporomandibular joint (TMJ), high molecular weight hyaluronic acid (HMHA), osteoarthritis (OA), fibrocartilage stem cells (FCSC), minute (min), and second (sec), enzyme linked immune assay (ELISA), 4-aminobutyraldehydediethylacetal (4-ABADA), 1-(3-dimethylaminopropyl)-3-ethylcarbodiimide hydrochloride (EDC), N-hydroxy succinimide (NHS), horseradish peroxidase (HRP), 3,3',5,5'-tetramethylbenzadine (TMB), Dulbecco's modified Eagle medium (DMEM), fetal bovine serum (FBS), ethylenediaminetetraacetic acid (EDTA), ribonucleic acid (RNA), deoxyribonucleic acid (DNA), complementary DNA (cDNA).

The compositions may be formulated for injectable administration using well-known carriers, as is understood in the art Pharmacologically acceptable carriers for various dosage forms are known in the art. For example, excipients, lubricants, binders, and disintegrants for solid preparations are known; solvents, solubilizing agents, suspending agents, isotonicity agents, buffers, and soothing agents for liquid preparations are known. In some embodiments, the pharmaceutical compositions include one or more additional components, such as one or more preservatives, antioxidants, stabilizing agents and the like. See: Remington—The Science and Practice of Pharmacy, $21^{st}$ ed., Lippincott (2006), which is incorporated herein in its entirety.

In one aspect of the invention, disclosed herein is a method of treating TMJ degeneration (including TMJ osteoarthritis, in a patient in need of such treatment which comprises administering to said patient a therapeutically-effective amount of a composition of the invention.

The following examples are given to illustrate the present invention. It should be understood, however, that the invention is not to be limited to the specific conditions or details described in the example. All printed publications referenced herein are specifically incorporated by reference.

Experimental

1) Synthesis of High Molecular Weight Hyaluronic Acid-Sclerostin Hydrogel

The following materials were used in the synthesis: sodium high molecular weight hyaluronate (HA) (average molecular weight 2000 kDa) (Life Biomedical, catalog #: HA2M), 3% BSA PBS, sclerostin (SOST) (R&D systems, catalog #: 1406-ST-025/CF), 1 ml Syringes, (BD Tuberculin Syringes, 14-826-87), 5 ml Falcon round bottom proplylene tube (Fisher scientific, catalog #: 14-959-11A), Instant Sealing Sterilization Pouch (FisherBrand, #01-812-54)

3% BSA PBS preparation: 1.5 g BSA was dissolved in 50 ml of sterile PBS and sterile filtered using a 0.45 um pore syringe filter in TC hood to yield a 3% BSA in PBS solution.

2% sclerostin HMW HA hydrogel and control preparation: SOST was reconstituted by adding 25 ug SOST to 125 ul of 3% BSA/PBS prepared as above to yield a 200 ug/ml SOST solution. An amount of 0.06 g HMW HA was dissolved in 3 ml of the SOST solution prepared above by vortexing and was then allowed to stand at 4° C. until fully dissolved. For the HMW HA control, 0.06 g HMW HA was dissolved in 3 ml 3% BSA PBS by vortexing and was allowed to stand at 4° C. until fully dissolved. For the SOST control, 22.5 ul of the 200 ug/ml reconstituted SOST prepared in step 1 above was dissolved in 3 ml 3% BSA PBS. Low molecular weight HA compositions were prepared similarly.

The above preparations yielded the following test groups evaluated below:
Vehicle: 0.1 ml 3% BSA PBS
SOST: 0.1 ml 1.5 ug/ml SOST. 22.5 ul×(200 ug/ml SOST reconstitution)/3 ml of 3% BSA PBS
HMW HA: 0.1 ml 2% HA. (0.06 g HMW HA in 3 ml 3% BSA PBS)
HMW HA-SOST: 0.1 ml 2 ug/ml SOST in HMW HA. (0.06 g HMW HA in 3 ml of 2 ug/ml of SOST).

2) Synthesis of PLGA microspheres (encapsulated with SOST): 250 mg of 50:50 PLGA (Sigma) was dissolved in 1 ml dichloromethane. On hundred ml of 2% isopropanol was prepared by dissolving 2 ml isopropanol in 98 ml distilled water. One ml of the PLGA solution prepared above was mixed with 10 ug sclerostin in 50 ul PBS and vortexed for 1 min at high speed. Two ml of 1% aqueous PVA was mixed into the above-prepared PLGA/PBS solution, vortexed for 1 min, and the resulting mixture added to 100 ml of 0.1% PVA in a hood with stirring at 450 rpm. To the resulting composition was added 100 ml of the 2% isopropanol and the whole stirred for 2 hours, following which the whole as filtered to collect the microspheres, which were washed three times with distilled water, collected in a 50 ml tube and stored in liquid nitrogen for 30 min, yielding SOST encapsulated in PLGA microspheres. Finally, the microspheres were freeze dried and stored at −20° C.

3) Preparation of conjugated HMW HA-SOST (shown in FIG. 6): 50 mg of high molecular weight hyaluronic acid sodium salt (HA) (Life Biomedical, catalog #: HA2M), was dissolved in 20 ml of distilled water at 4° C. and stored at 4° C. for twelve hours. The above HA solution was transferred into a small beaker, to which was added with stirring 7.2 mg of 1-(3-dimethylaminopropyl)-3-ethylcarbodiimide hydrochloride (EDC), 4.4 mg of N-hydroxy succinimide (NHS), and 6.56 mg of 4-aminobutyraldhydiethylacetal (4-ABADA) Stirring was continued for an additional 18 hours. The resulting solution was transferred into 15 ml Eppendof Centrifuge tubes and 10 ml of absolute ethanol was added. After centrifuging for 10 min at 3000 rpm, the supernatant was decanted and the gel-like solid was washed with 75-25 ethanol/water solution, centrifuged again and the remaining supernatant carefully decanted. The remaining solid was washed with 50-50 ethanol/water solution, centrifuged for a third time and the supernatant decanted off. The resulting material was lyophilized. One mg of aldehydized lyophilized HA was dissolved in 1 ml of 0.01 M of phosphoric acid and the resulting solution diluted 50 times with 0.01 M of phosphoric acid to yield hydrolyzed HA. To 5 ml of the hydrolyzed HA was added with stirring 5 μg of sclerostin and 1 mg $NaBH_3CN$, the pH of the resulting composition was adjusted to 6.0 with 2M NaOH solution, and stirring continued for 24 hours, following which the resulting material was lyophilized Evaluation Sclerostin-hyaluronic acid hydrogel and sclerostin release curve. Sclerostin (1 μg, R & D 1406-ST/CF) was mixed in 2% high molecular weight hyaluronic acid (HMW HA, 2000 kDa, Lifecore Biomedical) or in 2% and 3% low molecular weight (LMW HA, 500 KDa, Lifecore Biomedical) following the procedure described above. The hydrogels were placed onto a 12 mm Transwell® with 0.4 μm Pore Polyester Membrane Insert (Fisher Scientific, 07-200-161) and incubated in PBS in a 12-well plate at 37° C. The concentration of sclerostin was measured at each indicated time point using the quantitative sandwich enzyme immunoassay technique following manufacturer's instructions to plot the cumulative release curves. Briefly, standard or sample (100 μL) was added to each well and incubated for 2 h at 37° C., followed by treatment with primary antibody using either biotinylated anti-human Sclerostin antibody for 1 h at 37° C. For antibody detection, 100 μL of HRP-Avidin was for 1 h at 37° C. After washing, TMB substrate was added to each well for 15-30 min at 37° C., followed by the addition of 50 μL of Stop Solution. The optical density (OD) of each well was determined using a microplate reader at 450 nm. The Sclerostin concentrations were calculated by comparing the OD of each sample to the standard curve.

As shown in FIG. 1, the high molecular weight hyaluronic acid—sclerostin hydrogel exhibited sustained release of sclerostin over the 42 day test period, while the compositions with low molecular weight hyaluronic acid quickly released substantially all their sclerostin over only a few days. As shown in FIG. 7, the sclerostin released from the high molecular weight hyaluronic acid-sclerostin hydrogel showed no degradation after incubation at 37° C. for three weeks. This sustained release of sclerostin and the stability of the sclerostin over a prolonged period at 37° C. was unexpected and surprising. Sclerostin is normally stored at reduced temperatures to avoid possible decomposition, as advised by the supplier. The product data sheet specifies stability of the reconstituted material for 1 month at 2 to 8° C.

PLGA encapsulated sclerostin release curve. The PLG sclerostin microspheres prepared above were placed on Transwells in PBS at 37° C. and the concentration of sclerostin was measured at periods of time using a sclerostin human ELISA kit (Thermofisher) according to the manufacturer's instructinos. The calculated release curve is shown in FIG. 2, which indicates that the PLGA sclerostin microspheres gave sustained release of sclerostin over a 29 day period.

Conjugated sclerostin-HA release curve. Ten μg covalently linked HA-SOST was dissolved in 0.5 ml PBS. At each indicated time point shown in FIG. 8, 0.25 ml of solution was removed and replaced with an equal amount of PBS. Ten μl of each removed sample was diluted in 200 μl diluent buffer from an ELISA kit (Thermofisher) and the sclerostin content measured using the sclerostin human ELISA kit (Thermaofisher). The results are shown in FIG. 8, which indicates the sustained release of sclerostin from the sclerostin-linker hyaluronic acid over a period of 30 days.

Fibrocartilage stem cell (FCSC) isolation and culture. TMJ fibrocartilage was dissected from 8 week old Sprague Dawley rats and was digested with dispase II/collagenase I (4 mg/ml, 3 mg/ml) and shook at 37 degrees Celsius. Every 20 minutes cells were collected until all fibrocartilage tissues were digested. Single cell suspensions of fibrocartilage stem cells were cultured (5% $CO_2$, 37° C.) in basal medium consisting of DMEM (Invitrogen 11885-092) supplemented with 20% lot-selected fetal bovine serum (FBS, Gibco ES Cell FBS, 10439-024), glutamax (Invitrogen 35050-061), penicillin-streptomycin (Invitrogen 15140-163), and 100 mM 2-mercaptoethanol (Gibco) for 4-6 days. Cells were detached with trypsin-EDTA (GIBCO) and plated at P1. FCSCs in media containing 2% FBS were treated for 2, 7 and 10 days with trans-well containing either sclerostin mixed in 2% high molecular weight hyaluronic acid (HMW HA), 2% HMW-HA alone, Sclerostin (50 ng/ml), or PBS.

As shown in FIG. 3, the high molecular weight hyaluronic acid—sclerostin hydrogel induces differentiation of rat FCSCs but does not cause inflammation, as measured by levels of TNF-α and IL-1β. As shown in FIG. 4, the high molecular weight hyaluronic acid—sclerostin hydrogel induced FCSCs to differentiate into cartilage and reduces inflammation compared to sclerosin alone.

RNA Isolation and qRT-PCR. Total RNA was purified from fibrocartilage stem cells (Invitrogen 12183018A) and treated with DNAse I (Ambion AM2222) to remove genomic DNA. RNA quantity and purity was determined using Nanodrop. RNA samples (260/280>1.8) were used to obtain cDNA (Biorad AM2222). Quantitative RT-PCR was performed using SYBR Green PCR Master Mix (Applied Biosystems 4309155) using rat primers for Acan, Runx2, Axin2, Wnt3a, TNF-α, ILβ. Gene expression levels were normalized to housekeeping gene Gapdh. Results are shown in FIGS. 3 and 4.

Rabbit TMJ Injury Model. TMJ injury was surgically induced bilaterally in a total of 13 New Zealand white rabbits 3-4 months old. An oblique incision was created superior to the zygomatic process. Tissue was elevated and retracted to access the TMJ superior joint space and the disc was retracted posteriorly. A periosteal elevator was placed under the disc to protect the condyle from injury. A punch biopsy was used to create a 2.5 mm perforation in the lateral portion of the TMJ disc. No disc attachments were severed and the disc reduced to its normal anatomical location upon release of disc retraction. Rabbits were treated with unilateral HA-sclerostin hydrogel and HA injections on contralateral sides every other week (n=3) or once a month (n=4) and unilateral Sclerostin and PBS injections on contralateral sides every other week (n=3) or once a month (n=3). All rabbits were sacrificed after 8 weeks.

As shown in FIG. 5, the high molecular weight hyaluronic acid-sclerostin hydrogel healed TMJ disc perforation in a rabbit injury model, which is predictive of effects in humans. See: Embree, et al.—"Soft tissue ossification and condylar cartilage degeneration following TMJ disc perforation in a rabbit pilot study" Osteoarthritis Cartilage. 2015 April; 23(4):629-639, doi:10.1016j.joca.2014.12.015, which is incorporated herein in its entirety.

Although the compositions and methods of the invention have been described in the present disclosure by way of illustrative examples, it is to be understood that the invention is not limited thereto and that variations can be made as known by those skilled in the art without departing from the teachings of the invention defined by the appended claims.

What is claimed is:

1. A composition for treatment of temporomandibular joint degeneration comprising a hydrogel of sclerostin and high molecular weight hyaluronic acid, wherein the average molecular weight of the hyaluronic acid is from 1500±150 kDa to 4000±400 kDa.

2. The composition of claim 1 wherein the concentration of sclerostin is from 5±0.5 ng/100 µl to 1±0.1 mg/100 µl of the composition and the concentration of high molecular weight hyaluronic acid is from 0.1±0.01 wt % to 10±1 wt %.

3. The composition of claim 1 which consists essentially of sclerostin and high molecular weight hyaluronic acid.

4. The composition of claim 2 which consists essentially of sclerostin and high molecular weight hyaluronic acid.

5. The composition of claim 1 wherein the average molecular weight of the hyaluronic acid is 2000±200 kDa.

6. A method for treating temporomandibular joint degeneration in a patient in need of such treatment which comprises administering to said patient a therapeutically-effective amount of a composition selected from the composition of claim 1.

7. A method for treating temporomandibular joint degeneration in a patient in need of such treatment which comprises administering to said patient a therapeutically-effective amount of a composition selected from the composition of claim 3.

* * * * *

UNITED STATES PATENT AND TRADEMARK OFFICE
CERTIFICATE OF CORRECTION

PATENT NO. : 11,819,536 B2
APPLICATION NO. : 17/253993
DATED : November 21, 2023
INVENTOR(S) : Mildred Embree and Mo Chen It is certified that error appears in the above-identified patent and that said Letters Patent is hereby corrected as shown below:

In the Specification

Column 1, Lines 19-20, delete "This invention was made with government support under DE022060 awarded by the National Institutes of Health." and insert therein --This invention was made with government support under DE028215 and DE022060 awarded by the National Institutes of Health.--

Signed and Sealed this
Twenty-sixth Day of March, 2024

Katherine Kelly Vidal
Director of the United States Patent and Trademark Office